US011149038B2

(12) United States Patent
Gur et al.

(10) Patent No.: US 11,149,038 B2
(45) Date of Patent: Oct. 19, 2021

(54) SYNTHETIC CO-CRYSTALS OF ANHYDROUS GUANINE AND PROCESS FOR PREPARING THE SAME

(71) Applicant: Dvir Gur, Rehovot (IL)

(72) Inventors: Dvir Gur, Rehovot (IL); Lia Addadi, Rehovot (IL); Stephen Weiner, Rehovot (IL)

(73) Assignee: Dvir Gur, Rehovot (IL)

( * ) Notice: Subject to any disclaimer, the term of this patent is extended or adjusted under 35 U.S.C. 154(b) by 116 days.

(21) Appl. No.: 16/311,700

(22) PCT Filed: Jun. 21, 2017

(86) PCT No.: PCT/IL2017/050687
§ 371 (c)(1),
(2) Date: Dec. 20, 2018

(87) PCT Pub. No.: WO2017/221245
PCT Pub. Date: Dec. 28, 2017

(65) Prior Publication Data
US 2019/0211016 A1 Jul. 11, 2019

(30) Foreign Application Priority Data
Jun. 21, 2016 (IL) .......................... 246428

(51) Int. Cl.
*C07D 473/18* (2006.01)
(52) U.S. Cl.
CPC ........ *C07D 473/18* (2013.01); *C07B 2200/13* (2013.01)
(58) Field of Classification Search
CPC .................. C07D 473/18; C07B 2200/13
See application file for complete search history.

(56) References Cited

U.S. PATENT DOCUMENTS

| | | | |
|---|---|---|---|
| 3,557,113 A | 1/1971 | Yamada Toshitaka | |
| 3,692,768 A | 9/1972 | Takata | |
| 3,728,329 A | 4/1973 | Yano | |
| 2006/0005742 A1 | 1/2006 | Moeschl | |

FOREIGN PATENT DOCUMENTS

| | | | |
|---|---|---|---|
| DE | 1930265 A1 | 12/1969 | |
| DE | 102009044637 A1 * | 6/2011 | ............... A61Q 1/10 |
| DE | 102009044637 A1 | 6/2011 | |
| FR | 2010977 A1 | 2/1970 | |
| WO | 2004035692 A1 | 4/2004 | |
| WO | 2014097134 A1 | 6/2014 | |

OTHER PUBLICATIONS

Chester, Mikulski. Inorganica Chimica Acta, 108 (1985) L35-L37. (Year: 1985).*
DE 102009044637 English language translation (Year: 2011).*
Madden, J. J. Acta Cryst. (1973) B29, 914-915. (Year: 1973).*
Levy-Lior et al., (2010) Guanine-Based Biogenic Photonic-Crystal Arrays in Fish and Spiders. Adv Funct Mater 20: 320-329.
Pfaff; "Chapter 7.2.2.1 Natural Pearl Essence". In: "High Performance Pigments". 2002, Wiley-VCH, Wenheim (DE), pp. 2, 103-104, 121 XP055775454.
Title 21—Food and Drugs; Chapter I—Food and Drug Administration, Department of Health and Human Services. Subchapter A—General; Part 73—Listing of Color Additives Exempt from Certification. Subpart B—Drugs; Sec. 73.1329 Guanine. Retrieved from: https://www.accessdata.fda.gov/scripts/cdrh/cfdocs/cfcfr/CFRSearch.cfm? fr=73.1329&SearchTerm=guanine, on Feb. 21, 2021 [Revised as of Apr. 1, 2020]. 2 pages.
Kossel and Gross (1924) Über die Darstellung und quantitative Bestimmung des Arginins. Hoppe-Seyler's Zeitschrift Fuer Physiologische Chemie 135(1-4): 167-174. With machine translation.
Levy-Lior et al., (2008) Biogenic Guanine Crystals from the Skin of Fish May Be Designed to Enhance Light Reflectance. Crystal Growth & Design 8(2): 507-511.
Madden (1973) The unit cell of a mixed crystal of guanine and 8-azaguanine. Acta Crystallographica Section B 29(4): 914-915.
Meisenheimer (1921) Die stickstofthaltigen Bestandteile der Hefe. II. Mitteilung. Die Purinbasen und Diaminosäuren. Ergebnisse. Hoppe-Seyler's Zeitschrift Fuer Physiologische Chemie 114(5-6): 205-249. With machine translation.
Mikulski et al., (1985) Cobalt(II), copper(II) and zinc(II) chloride complexes involving both neutral and monoanionic guanine ligands. Inorganica Chimica Acta 108(4): L35-L37.
Pfleiderer (1961) Purine, IV. Ober die Methylierung des 9-Methylguanins und die Struktur des Herbipolins. Justus Liebigs Annalen der Chemie 647(1): 167-173. With machine translation.
Thewalt et al., (1971) The crystal structure of guanine monohydrate. Acta Crystallographica Section B 27(12): 2358-2363.
Weiss and Venner (1965) Das komplexchemische Verhalten von Pyrimidinabkömmlingen, IV. Das komplexchemische Verhalten von Hydroxypurinen gegenüber Kupfer(II). Hoppe-Seyler's Zeitschrift Fuer Physiologische Chemie 340: 138-147. English summary on p. 147.
Zhe-Long Jin et al., (2005) Constituents of fish scale foil, a natural food colorant. Nihon Shokuhin Kagaku Gakkaishi—Japanese Journal of Foodchemistry, Nihon Shokuhin Kagaku Gakkai 12(2): 85-87. Abstract.
Database Reaxys [Online]; Reed Elsevier Properties SA, XP002773266. Database accession No. 4930625 (Reaxys ID).

* cited by examiner

*Primary Examiner* — Deepak R Rao
(74) *Attorney, Agent, or Firm* — J.A. Lindeman & Co., PLLC

(57) ABSTRACT

This invention is directed to synthetic co-crystals of anhydrous guanine and at least one additional material, wherein the co-crystals have a high refraction index and therefore, provide products with pearlescence or whiteness with high coverage. The invention is further directed to a process for the preparation of anhydrous guanine and of the co crystals.

32 Claims, 8 Drawing Sheets

SYNTHETIC CO-CRYSTALS OF ANHYDROUS GUANINE AND PROCESS FOR PREPARING THE SAME

CROSS-REFERENCE TO RELATED APPLICATIONS

National Phase Application of PCT International Application No. PCT/IL2017/050687, International Filing Date Jun. 21, 2017, claiming priority of IL Patent Application No. 246428, filed Jun. 21, 2016, which are all hereby incorporated by reference.

FIELD OF THE INVENTION

This invention is directed to synthetic co-crystals of anhydrous guanine and at least one additional material, wherein the co-crystals have a high refraction index and therefore, provide products with pearlescence or whiteness with high coverage. The invention is further directed to a process for the preparation of anhydrous guanine and of the co crystals.

BACKGROUND OF THE INVENTION

Some of the most brilliant colors in nature are produced by the interaction of light with structured materials, causing light scattering or reflection. Such structured materials, appearing alone or together with various types of pigmentation, are widespread in nature. Further, the industrial use of natural and synthetic structured materials is known.

Guanine is a common mineralized material appearing in nature that is known to produce structural colors. Systems based on intracellular arrays of very thin guanine nanocrystals are found in a variety of marine and terrestrial animals, such as fish, spiders, butterflies, mollusks, copepods and chameleons. There are three different known phases of crystalline guanine, namely, guanine monohydrate and two polymorphs of anhydrous guanine, $\alpha$ and $\beta$; however, only anhydrous guanine was reported to be present in biogenic systems. Anhydrous guanine is known to have an exceptionally high refractive indexes, i.e., n=1.83 and 1.81, in the reflected direction, which is extraordinarily high not only relative to organic crystals, but also to many inorganic materials (e.g., water n=1.33, cellulose n=1.50, mica n=1.60). The high refractive index of guanine is due to its crystalline structure consisting of very dense layers of hydrogen bonded guanine molecules stacked by $\pi$-$\pi$ interactions.

Due to its high refractive index, the optical properties of anhydrous guanine are beneficial for industry and since it is non-hazardous it is incorporated into a variety of applications and artificial systems, such as cosmetics, coatings and jewelry. Recent studies have looked into the incorporation of guanine into sophisticated systems that will also provide dynamic control over crystal orientation, providing the system with ability to tune reflectivity. The anhydrous guanine crystals used today are extracted from biological specimens, namely fish scales. The guanine crystals extracted from fish are known for their natural soft and silky appearance. Recent studies have shown that reducing the size of the crystals by milling can dramatically improve their covering power coverage (WO2014/097134). Fish scales contain less than 1% guanine crystals and the process of isolation and purification is complex and costly. Furthermore, varying crystal dimensions, morphologies and the quality of biogenic guanine crystals, renders natural anhydrous guanine difficult for use in modern industry. Impurities in isolated fish crystals result in yellowish color and fishy odor, which is undesirable. However, the preparation of synthetic anhydrous guanine is complicated since the guanine is insoluble in most solvents and since it has been proven to be difficult to prepare crystals with the desired morphology, which provides the necessary high refractive index.

The main reasons impeding the industrial use of synthetic anhydrous guanine crystals are guanine insolubility in most solvents, and the difficulty of obtaining crystals in the desired thickness and width for the plate morphology, such that the plane perpendicular to the high refractive index direction is dominant. In this respect it is noted that a plate morphology is defined by having two dimensions at least 5 times longer than the third dimension. Although several methods for preparing synthetic guanine are known in the art, none of them are applicable industrially, due to the complexity of the process, lack of reproducibility, the poor quality of the product, or combination thereof.

SUMMARY OF THE INVENTION

In one embodiment, this invention is directed to synthetic co-crystals comprising anhydrous guanine and at least one additional material. In another embodiment, the at least one additional material is selected from the group comprising purines, pteridine, pyrimidine, derivatives thereof or nucleosides thereof. In another embodiment, the co-crystals of this invention have a plate morphology. In another embodiment, the synthetic co-crystals have a refractive index between 1.65-1.95.

In one embodiment, this invention is directed to a pH controlled process for preparing synthetic co-crystals of anhydrous guanine and at least one additional material, wherein said process comprises the steps of:
 preparing a basic or acidic aqueous solution of guanine and at least one additional material;
 maintaining the basic or acidic aqueous solution at a predetermined temperature range for a predetermined period of time;
 filtering the basic or acidic aqueous solution to provide a filtrate;
 adjusting the pH of the filtrate by adding a base or an acid to the filtrate over a predefined period of time until a predetermined pH value is obtained, thereby providing a synthetic co-crystal suspension comprising co-crystals;
 allowing the synthetic co-crystal suspension to mature over a predetermined period of time; and
 collecting the synthetic co-crystals from the crystal suspension.

In another embodiment, the molar ratio between the additional material and the guanine is between 4:1-0.01:1. In another embodiment, the basic or acidic aqueous solution comprises 0.003-0.2M of guanine. In another embodiment, the basic or acidic aqueous solution comprises 0.003-0.2M of at least one additional material. In another embodiment the pH of the acidic solution is between 0-3; and the pH of the basic solution is between 12-14.

In one embodiment, this invention is directed to synthetic co-crystals of anhydrous guanine and at least one additional material, prepared according to a pH controlled process comprising the steps of:
 preparing a basic or acidic aqueous solution of guanine and at least one additional material;

maintaining the basic or acidic aqueous solution at a predetermined temperature range for a predetermined period of time;

filtering the basic or acidic aqueous solution to provide a filtrate;

adjusting the pH of the filtrate by adding a base or an acid to the filtrate over a predefined period of time until a predetermined pH value is obtained, thereby providing a synthetic co-crystal suspension comprising co-crystals;

allowing the synthetic co-crystal suspension to mature over a predetermined period of time; and collecting the synthetic co-crystals from the crystal suspension.

In one embodiment, this invention is directed to a temperature controlled process for preparing synthetic co-crystals of anhydrous guanine and at least one additional material, wherein said process comprises the steps of:

preparing a basic or acidic aqueous solution of guanine and at least one additional material;

heating the basic or acidic aqueous solution to a predetermined temperature for the predetermined length of time;

inducing co-crystallization by cooling the basic or acidic aqueous solution at a predetermined rate until reaching a predetermined temperature thereby providing a synthetic co-crystal suspension comprising crystals;

allowing the synthetic co-crystal suspension to mature over a predetermined period of time; and collecting the synthetic co-crystals from the crystal suspension.

In one embodiment, this invention is directed to synthetic co-crystals of anhydrous guanine and at least one additional material, prepared according to a temperature controlled process comprising the steps of:

preparing a basic or acidic aqueous solution of guanine and at least one additional material;

heating the basic or acidic aqueous solution to a predetermined temperature for the predetermined length of time;

inducing co-crystallization by cooling the basic or acidic aqueous solution at a predetermined rate until reaching a predetermined temperature thereby providing a synthetic co-crystal suspension comprising crystals;

allowing the synthetic co-crystal suspension to mature over a predetermined period of time; and collecting the synthetic co-crystals from the crystal suspension.

In one embodiment, this invention is directed to a pH controlled process for the preparation of anhydrous guanine comprising the steps of:

preparing a basic or acidic aqueous solution of guanine;

maintaining the basic or acidic aqueous solution at a predetermined temperature range for a predetermined period of time;

filtering the basic or acidic aqueous solution to provide a filtrate;

adjusting the pH of the filtrate by adding a base or an acid to the filtrate over a predefined period of time until a predetermined pH value is obtained, thereby providing a guanine crystal suspension comprising crystals;

allowing the suspension to mature over a predetermined period of time; and collecting the anhydrous guanine crystals from the crystal suspension.

In one embodiment, this invention is directed to a temperature controlled process for the preparation of anhydrous guanine comprising the steps of:

preparing a basic or acidic aqueous solution of guanine;

heating the basic or acidic aqueous solution to a predetermined temperature for the predetermined length of time;

inducing crystallization by cooling the basic or acidic aqueous solution at a predetermined rate until reaching a predetermined temperature thereby providing a suspension comprising anhydrous guanine crystals;

allowing the anhydrous guanine suspension to mature over a predetermined period of time; and collecting the anhydrous guanine from the crystal suspension.

In one embodiment, this invention is directed to an anhydrous guanine prepared according to the temperature controlled process or the pH controlled process of this invention or to a combination of both.

In one embodiment, this invention is directed to synthetic co-crystal or anhydrous guanine prepared according to the process of this invention for use in paints, coatings, printing inks, plastics, cosmetic formulations, food products, paper, agricultural products, and medicaments.

In one embodiment, this invention is directed to paints, coatings, printing inks, plastics, cosmetic formulations, food products, paper, agricultural products, and medicaments comprising the synthetic co-crystal of this invention or the anhydrous guanine prepared according to the process of this invention.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings. Embodiments of the invention are illustrated by way of example and not limitation in the figures of the accompanying drawings, in which like reference numerals indicate corresponding, analogous or similar elements, and in which:

FIGS. 1A and 1B present elongated acicular (needle shaped) crystals of anhydrous guanine prepared in acidic conditions, while

FIG. 7A presents a light microscope image. FIG. 7B presents a light microscope image with crossed polarizers on. FIG. 7C presents FT-IR spectra.

FIG. 8A presents the chemical structure of guanine and hypoxanthine. FIG. 8B presents X-ray powder diffraction of guanine-hypoxathine crystals. FIG. 8C presents SEM image of guanine-hypoxathine crystals, showing a plate morphology.

DETAILED DESCRIPTION OF EMBODIMENTS OF THE INVENTION

Figure 1A:
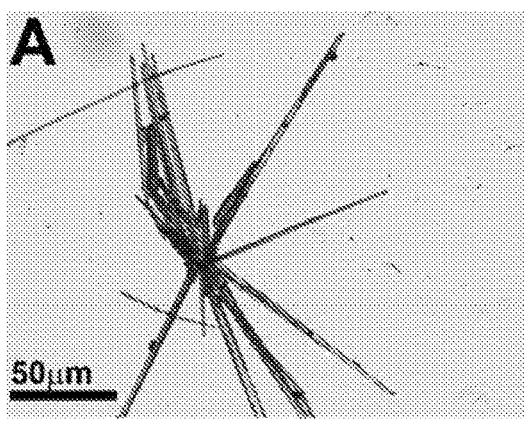

Embodiments of the invention are directed to synthetic co-crystals of anhydrous guanine and at least one additional material and to anhydrous guanine prepared according to the process of this invention. According to some embodiments, the synthetic co-crystals of the invention have a plate morphology in contrast to the bulky prismatic crystals of pure anhydrous guanine. According to some embodiments, the synthetic co-crystals have a preferred morphology which provides high refractive index. In another embodiment, the preferred morphology is a plate morphology. According to some embodiments, in a plate morphology, the co-crystals or the anhydrous guanine have a high surface to volume ratio, wherein the thickness of the co-crystals or the anhydrous guanine, which determines the pearlescence and/or the whiteness of the material, may be controlled by altering, e.g., the additive concentration, the pH, and/or the temperature.

The synthetic co-crystal comprises at least 50 mol % of guanine. In another embodiment, the synthesis co-crystal comprises at least 0.01 mol % of the additional material. According to some embodiments, the additive concentration may be altered between about 0.01-50 mol %. In another embodiment, the additive concentration is between 0.1 to 3 mol %. In another embodiment, the additive concentration is between 5 to 10 mol %. In another embodiment, the additive concentration is between 10 to 50 mol %. In another embodiment, the additive concentration is between 0.1 to 10 mol %. In another embodiment, the additive concentration is between 25 to 50 mol %.

In some embodiment, the concentration of the guanine and the additional material used in the preparation of the co-crystal is not the same concentration obtained in the co-crystal itself.

According to some embodiments, the structure of the guanine and the additional material is similar According to some embodiments, the additional material is a purine or a derivative thereof. According to some embodiments, the purine or the derivative thereof is hypoxanthine, xanthine, uric acid, isoguanine or theobromine. According to some embodiments, the additional material is pteridine or a derivative thereof. According to some embodiments, the pteridine derivative is isoxanthopterin or xanthopterin. According to some embodiments, the additional material is pyrimidine or a derivative thereof. According to some embodiments, the pyrimidine derivative is thymine, cytosine or uracil. According to some embodiments, the additional material is a nucleoside of a purine, pteridine or pyrimidine or a derivative thereof, including, though not limited to guanosine, cytidine, thymidine, uridine, adenosine and inosine. According to some embodiments, the co-crystals may include two or more additional materials.

In one embodiment, the co-crystal of this invention includes a guanine and another material. In another embodiment, the other material includes a purine, pteridine, pyrimidine, nucleoside of a purine, pteridine or pyrimidine; or derivative thereof. In another embodiments the derivatives includes between one to six substituents of the additional materials selected from the group consisting from keto, halo, cyano, amino, nitro, hydroxy, alkoxy, alkyl, alkenyl, aryl, cycloalkyl, heterocycloalkyl or combination thereof.

In another embodiment, the co-crystal of this invention includes anhydrous guanine and between 1-5 different additional materials. Each represents a separate embodiment of this invention.

Figure 8A:
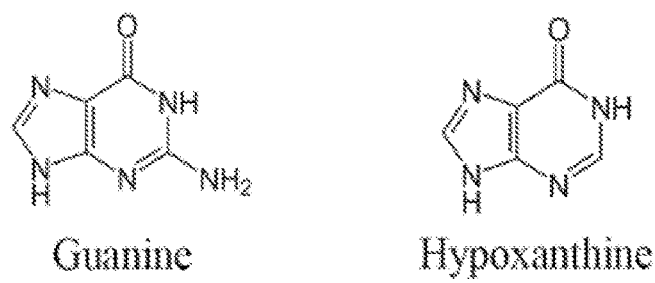
FIGS. 8A-8C present co-crystallization of guanine and hypoxanthine.
Figure 8B:
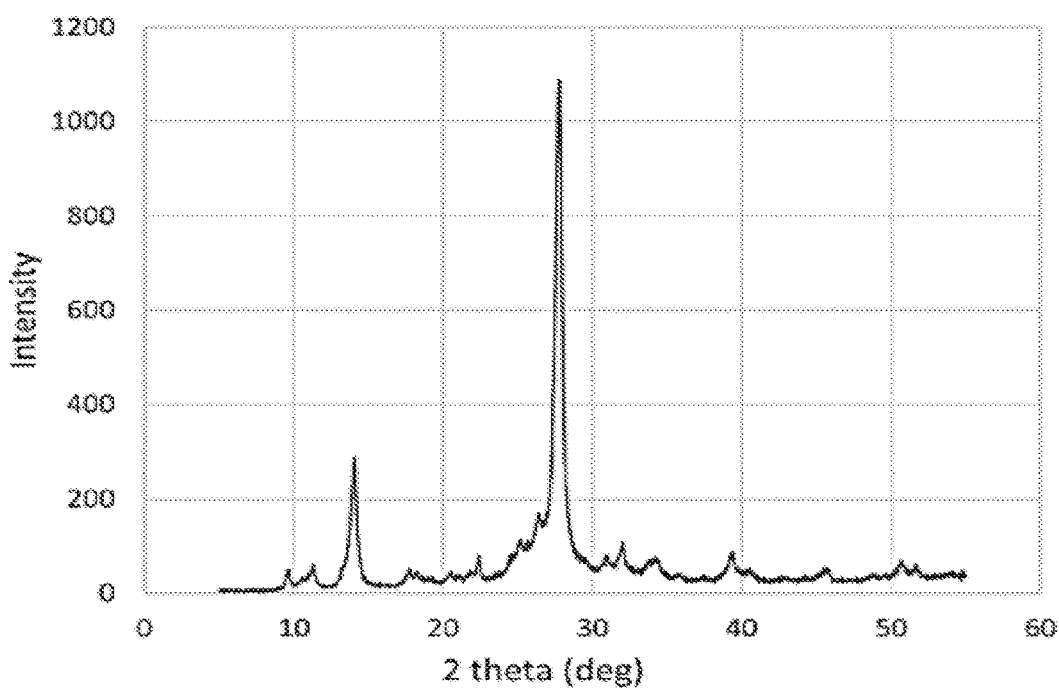
Figure 8C:
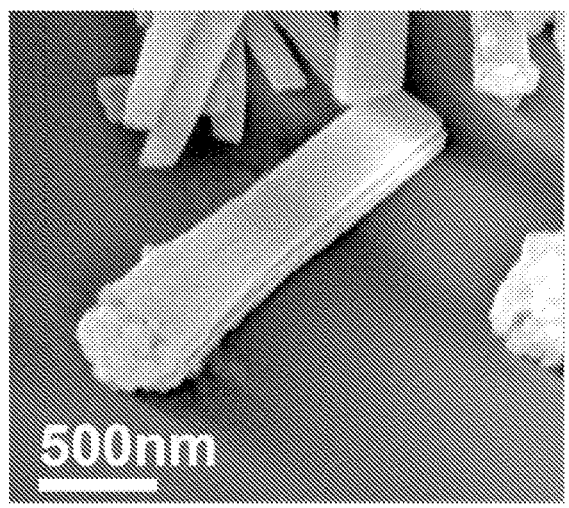

In another embodiment, the co-crystal of this invention includes a guanine and hypoxanthine in a plate morphology (FIG. 8C). In another embodiment, the co-crystal including the guanine and hypoxanthine in a plate morphology provides X-ray powder diffraction as presented in FIG. 8B.

According to some embodiments, the refractive index of the co-crystals is between about 1.65-1.95. In another embodiment, the refractive index of the co-crystals is between about 1.75-1.86. According to some embodiments, the crystals are about 5-250 μm long. According to some embodiments, the crystals are about 1-50 μm wide. According to some embodiments, the crystals are about 20-500 nm thick. According to some embodiments, the crystals have smooth surfaces, wherein smooth surfaces refers to a surface having an even and regular surface or consistency; free from perceptible projections, lumps, or indentations. In another embodiment, smooth surfaces are considered to be flat surfaces within a range of 1-10 nm. The morphology of the crystals is such as having a plane surface within a range of 1-10 nm. The dimensions of the crystals may be controlled by various conditions, such as the initial concentration of reactants, the temperature gradient during the process for forming the crystals, the initial pH, the final pH, the rate of pH adjustment during the process, the speed of stirring, the time during which the crystals are maintained in suspension, and the like.

Further embodiments of the invention are directed to a pH controlled process for preparing synthetic co-crystals of anhydrous guanine and at least one additional material, wherein said process comprises the steps of:
preparing a basic or acidic aqueous solution of guanine and at least one additional material;
maintaining the basic or acidic aqueous solution at a predetermined temperature range for a predetermined period of time;
filtering the basic or acidic aqueous solution to provide a filtrate;
adjusting the pH of the filtrate by adding a base or an acid to the filtrate over a predefined period of time until a predetermined pH value is obtained, thereby providing a synthetic co-crystal suspension comprising co-crystals;

allowing the synthetic co-crystal suspension to mature over a predetermined period of time; and collecting the synthetic co-crystals from the crystal suspension.

Further embodiments of the invention are directed to a pH controlled process for preparing anhydrous guanine, wherein said process comprises the steps of:

preparing a basic or acidic aqueous solution of guanine;

maintaining the basic or acidic aqueous solution at a predetermined temperature range for a predetermined period of time;

filtering the basic or acidic aqueous solution to provide a filtrate;

adjusting the pH of the filtrate by adding a base or an acid to the filtrate over a predefined period of time until a predetermined pH value is obtained, thereby providing a guanine crystal suspension comprising crystals;

allowing the suspension to mature over a predetermined period of time; and collecting the anhydrous guanine crystals from the crystal suspension.

In some embodiments, the anhydrous guanine prepared by the pH controlled process of this invention is a crystalline anhydrous guanine.

According to some embodiments, the pH of the processes is controlled in the reaction vessel, such that the guanine is protonated and deprotonated, affecting the solubility thereof in the basic or acidic aqueous solution. According to some embodiments, once the guanine is dissolved, the pH of the basic or acidic aqueous solution may be adjusted to induce crystallization, wherein the morphology of the produced crystals may be controlled by the particular pH used throughout the process.

According to some embodiments, the pH of the processes may be altered between about 7-13. According to some embodiments, the temperature may be altered between about 4-60° C. Further, as detailed herein, the thickness of the co-crystals may also be controlled by parameters influencing the crystal size, such as the initial concentration of reactants, temp the temperature gradient during the process for forming the crystals, the initial pH, the final pH, the rate of pH adjustments during the process, the time during which the crystals are maintained left in suspension, and the like, as detailed herein.

According to some embodiments, the molar ratio between the additional material and the guanine introduced into the reaction vessel of the process for preparing synthetic co-crystals is about 3:1. According to some embodiments, the molar ratio between the additional material and the guanine introduced into the reaction vessel is between about 4:1-0.01:1. In another embodiment, the molar ratio between the additional material and the guanine introduced into the reaction vessel is between about 4:1-1:1. In another embodiment, the molar ratio between the additional material and the guanine introduced into the reaction vessel is between about 4:1-0.5:1. In another embodiment, the molar ratio between the additional material and the guanine introduced into the reaction vessel is between about 4:1-0.1:1. In another embodiment, the molar ratio between the additional material and the guanine introduced into the reaction vessel is between about 4:1-0.05:1. According to some embodiments, the higher the solubility of the additional material, the higher the molar ratio between the additional material and the guanine.

According to some embodiments, the basic or acidic aqueous solution comprises about 0.003-0.2M of guanine. According to some embodiments, the basic or acidic aqueous solution comprises about 0.003-0.01M of guanine. According to some embodiments, the basic or acidic aqueous solution comprises about 0.01-0.05M of guanine. According to some embodiments, the basic or acidic aqueous solution comprises about 0.05-0.1M of guanine. According to some embodiments, the basic or acidic aqueous solution comprises about 0.1-0.2M of guanine.

According to some embodiments, the low concentration of guanine and/or the slow adjustment of pH, e.g., dropwise, induces fewer nucleation events and therefore, large crystals, having an average size of about 5-1000 µm of anhydrous guanine, are formed. In another embodiment, large crystals of anhydrous guanine having an average size of about 5-50 µm, are formed. In another embodiment, large crystals having an average size of about 10-100 µm, are formed. In another embodiment, large crystals having an average size of about 100-1000 µm, are formed. In another embodiment, large crystals having an average size of above 5-70 µm provide a strong pearlescent effect.

According to some embodiments, at high concentration of guanine, between about 0.1-0.2M, and when the pH is rapidly adjusted, e.g., by adding the acid/base in one dose, the formation of small crystals of anhydrous guanine, having an average size of about 0.01-10 µm, is induced. In another embodiment, small crystals having an average size of about 0.1-5 µm, are formed. In another embodiment, small crystals having an average size of about 1-10 µm, are formed. In another embodiment, small crystals having an average size of about 0.1-1 µm, are formed. In another embodiment, small crystals having an average size of less than 0.05-5 µm provide a whiteness with high coverage (non-interferential particles). In some embodiments, there is an overlap in the small and large crystal sizes because there isn't a clear cut in their optical properties; larger plate-like particles will have a tendency to cause interference and therefore pearlescence, small particles will have a tendency to produce whiteness.

According to some embodiments, the low concentration of guanine and the additional material and/or the slow adjustment of pH, e.g., dropwise, induces fewer nucleation events and therefore, large co-crystals, having an average size of about 5-1000 µm of the co-crystal. In another embodiment, large co-crystals having an average size of about 5-50 µm, are formed. In another embodiment, large crystals having an average size of about 10-100 µm, are formed. In another embodiment, large crystals having an average size of about 100-1000 µm, are formed. In another embodiment, large crystals having an average size of above 5-70 µm provide a strong pearlescent effect.

According to some embodiments, at high concentration of guanine and additional material, between about 0.1-0.2M, and when the pH is rapidly adjusted, e.g., by adding the acid/base in one dose, the formation of small crystals of co-crystals, having an average size of about 0.01-10 µm, is induced. In another embodiment, small crystals having an average size of about 0.1-5 µm, are formed. In another embodiment, small crystals having an average size of about 1-10 µm, are formed. In another embodiment, small crystals having an average size of about 0.1-1 µm, are formed. In another embodiment, small crystals having an average size of less than 0.05-5 µm provide a whiteness with high coverage (non-interferential particles). In some embodiments, there is an overlap in the small and large crystal sizes because there isn't a clear cut in their optical properties;

larger plate-like particles will have a tendency to cause interference and therefore pearlescence, small particles will have a tendency to produce whiteness.

According to some embodiments, the acid is any appropriate acid in an aqueous solution, such as HCl, $H_2SO_4$, $H_3PO_4$, $HNO_3$, $C_6H_8O_7$, $H_2CO_3$, $H_3BO_3$, or any combination thereof. It is noted that the concentrations of the acids may be determined by the required pH, and may be dependent on the Ka of the particular acid used, such that the stronger the acid, the lower the concentration thereof used.

According to some embodiments, the pH of the acidic solution is between about 0-3. According to some embodiments, the pH of the acidic solution is between about 0-1. According to some embodiments, the pH of the acidic solution is between about 1-2. According to some embodiments, the pH of the acidic solution is between about 2-3. According to some embodiments, the pH of the acidic solution is between about 0.5-1.5. According to some embodiments, the pH of the acidic solution is about 1.

According to some embodiments, the base is any appropriate base in aqueous solution, such as NaOH, $NaHCO_3$, KOH, $NH_4OH$, $Ca(OH)_2$, or any combination thereof. It is noted that the concentrations of the bases may be determined by the required pH, and may be dependent on the Kb of the particular base used, such that the stronger the base, the lower the concentration thereof used.

According to some embodiments, the pH of the basic solution is between about 12-14. According to some embodiments, the pH of the basic solution is between about 12-13. According to some embodiments, the pH of the basic solution is between about 13-14. According to some embodiments, the pH of the basic solution is between about 11.5-12.5. According to some embodiments, the pH of the basic solution is about 12.

According to some embodiments, the basic or acidic aqueous solution is maintained at a temperature of about 4-60° C. 10 min to 1 hour. According to some embodiments, the basic or acidic aqueous solution is maintained at a temperature of about 4-10° C. for a predetermined period of time. According to some embodiments, the basic or acidic aqueous solution is maintained at a temperature of about 10-20° C. for a predetermined period of time. According to some embodiments, the basic or acidic aqueous solution is maintained at a temperature of about 20-30° C. for a predetermined period of time. According to some embodiments, the basic or acidic aqueous solution is maintained at a temperature of about 30-40° C. for a predetermined period of time. According to some embodiments, the basic or acidic aqueous solution is maintained at a temperature of about 40-50° C. for a predetermined period of time. According to some embodiments, the basic or acidic aqueous solution is maintained at a temperature of about 50-60° C. for a predetermined period of time. According to some embodiments, the basic or acidic aqueous solution is maintained at a temperature of about 25° C. for a predetermined period of time.

As detailed herein, after maintaining the basic or acidic aqueous solution at a predetermined temperature for a predetermined period of time, the basic or acidic aqueous solution is filtered to provide a filtrate. According to some embodiments, the basic or acidic aqueous solution is filtered using a polyvinylidene difluoride filter or any other appropriate filter that is resistant to high alkalinity and high acidity, e.g., a polytetrafluoroethylene (PTFE) filter.

According to some embodiments, an acid or a base are added to the filtrate in order to ensure that the guanine and the additional material are dissolved. According to some embodiments, about 0.01 ml of a 0.1M basic or acidic solution, e.g., NaOH, $NaHCO_3$, KOH, $NH_4OH$, $Ca(OH)_2$, or any combination thereof, or HCl, $H_2SO_4$, $H_3PO_4$, $HNO_3$, $C_6H_8O_7$, $H_2CO_3$, $H_3BO_3$, or any combination thereof, solution, respectively, are added to ensure dissolution.

According to some embodiments, an acid or a base are added to the filtrate in order to ensure that the guanine is dissolved. According to some embodiments, about 0.01 ml of a 0.1M basic or acidic solution, e.g., NaOH, $NaHCO_3$, KOH, $NH_4OH$, $Ca(OH)_2$, or any combination thereof, or HCl, $H_2SO_4$, $H_3PO_4$, $HNO_3$, $C_6H_8O_7$, $H_2CO_3$, $H_3BO_3$, or any combination thereof, solution, respectively, are added to ensure dissolution.

According to some embodiments, the co-crystallization is induced by adjusting the pH of the filtrate, thereby providing a co-crystal suspension. According to some embodiments, the pH is adjusted by adding a base, e.g., NaOH, $NaHCO_3$, KOH, $NH_4OH$, $Ca(OH)_2$, or any combination thereof, or an acid, e.g., HCl, to the solution at a predefined rate over a predefined period of time.

According to some embodiments, the crystallization is induced by adjusting the pH of the filtrate, thereby providing a crystal suspension. According to some embodiments, the pH is adjusted by adding a base, e.g., NaOH, $NaHCO_3$, KOH, $NH_4OH$, $Ca(OH)_2$, or any combination thereof, or an acid, e.g., HCl, to the solution at a predefined rate over a predefined period of time.

According to some embodiments the pH of the added base is about 12-14. According to some embodiments the pH of the added base is about 12-13. According to some embodiments the pH of the added base is about 13-14.

According to some embodiments, the pH of the added acid is about 0-3. According to some embodiments, the pH of the added acid is about 0-1. According to some embodiments, the pH of the added acid is about 1-2. According to some embodiments, the pH of the added acid is about 2-3.

According to some embodiments, the pH is adjusted by adding an acid or a base dropwise. According to some embodiments, the base or acid are added to the filtrate over a predefined period of time of about 1-20 minutes. According to some embodiments, the base or acid are added to the filtrate over a predefined period of time of about 1-5 minutes. According to some embodiments, the base or acid are added to the filtrate over a predefined period of time of about 5-10 minutes. According to some embodiments, the base or acid are added to the filtrate over a predefined period of time of about 10-15 minutes. According to some embodiments, the base or acid are added to the filtrate over a predefined period of time of about 15-20 minutes.

According to some embodiments, the pH is adjusted by adding a predetermined amount of an acid or a base in one dose. In another embodiment, the pH of the reaction mixture is adjusted by evaporating a volatile material (for example ammonia, if used as a base). Any change in the concentration of the materials in the reaction mixture, affects the pH of the reaction mixture.

According to some embodiments, the pH of the filtrate is adjusted until a predefined pH value is obtained. According to some embodiments, the pH of the filtrate is monitored throughout the adjustment of the pH using a pH meter. According to some embodiments, the predefined pH value is about 1-13. According to some embodiments, the predefined pH value is about 1-2. According to some embodiments, the predefined pH value is about 2-3. According to some embodiments, the predefined pH value is about 3-4. According to some embodiments, the predefined pH value is about 4-5. According to some embodiments, the predefined pH value is about 5-6. According to some embodiments, the predefined pH value is about 6-7. According to some embodiments, the predefined pH value is about 7-8. According to some embodiments, the predefined pH value is about 8-9. According to some embodiments, the predefined pH value is about 9-10. According to some embodiments, the predefined pH value is about 10-11. According to some embodiments, the predefined pH value is about 11-12. According to some embodiments, the predefined pH value is about 12-13. According to some embodiments, the predefined pH value is about 10.5-11.5. According to some embodiments, the predefined pH value is about 11.

As detailed herein, the pH adjustment provides a co-crystal suspension. The co-crystal suspension may be allowed to mature for a predefined period of time. According to some embodiments, the co-crystal suspension is allowed to mature for about 1 minute to 1 week. According to some embodiments, the co-crystal suspension is allowed to mature for about 0.2-24 hours. According to some embodiments, the co-crystal suspension is allowed to mature for about 0.2-1 hours. According to some embodiments, the co-crystal suspension is allowed to mature for about 1-6 hours. According to some embodiments, the co-crystal suspension is allowed to mature for about 6-12 hours. According to some embodiments, the co-crystal suspension is allowed to mature for about 12-24 hours. Once matured, the co-crystals may be collected from the crystal suspension by any appropriate means. According to some embodiments, a shorter maturing time provides smaller crystals than a longer maturing time, as long as no other parameters are changed.

As detailed herein, the pH adjustment provides a crystal suspension. The crystal suspension may be allowed to mature for a predefined period of time. According to some embodiments, the crystal suspension is allowed to mature for about 1 minute to 1 week. According to some embodiments, the crystal suspension is allowed to mature for about 0.2-24 hours. According to some embodiments, the crystal suspension is allowed to mature for about 0.2-1 hours. According to some embodiments, the crystal suspension is allowed to mature for about 1-6 hours. According to some embodiments, the crystal suspension is allowed to mature for about 6-12 hours. According to some embodiments, the crystal suspension is allowed to mature for about 12-24 hours. Once matured, the crystals may be collected from the crystal suspension by any appropriate means. According to some embodiments, a shorter maturing time provides smaller crystals than a longer maturing time, as long as no other parameters are changed.

Further embodiments of the invention are directed to a temperature controlled process for preparing synthetic co-crystals of anhydrous guanine and at least one additional material, wherein said process comprises the steps of:
preparing a basic or acidic aqueous solution of guanine and at least one additional material;
heating the basic or acidic aqueous solution to a predetermined temperature for the predetermined length of time;
inducing co-crystallization by cooling the basic or acidic aqueous solution at a predetermined rate until reaching a predetermined temperature thereby providing a synthetic co-crystal suspension comprising crystals;
allowing the synthetic co-crystal suspension to mature over a predetermined period of time; and
collecting the synthetic co-crystals from the crystal suspension.

Further embodiments of the invention are directed to a temperature controlled process for preparing anhydrous guanine, wherein said process comprises the steps of:
preparing a basic or acidic aqueous solution of guanine;
heating the basic or acidic aqueous solution to a predetermined temperature for the predetermined length of time;
inducing crystallization by cooling the basic or acidic aqueous solution at a predetermined rate until reaching a predetermined temperature thereby providing a suspension comprising anhydrous guanine crystals;
allowing the anhydrous guanine suspension to mature over a predetermined period of time; and
collecting the anhydrous guanine from the crystal suspension.

In some embodiments, the anhydrous guanine prepared by the temperature controlled process of this invention is a crystalline anhydrous guanine.

It is noted that since the changes in the solubility of the guanine and the additional material obtained by changing the temperature in the temperature controlled process for preparing co crystals are smaller than the changes obtained by changing the pH, the concentration ranges in the temperature controlled process may be smaller.

It is noted that since the changes in the solubility of the guanine obtained by changing the temperature in the temperature controlled process for preparing anhydrous guanine crystals are smaller than the changes obtained by changing the pH, the concentration ranges in the temperature controlled process may be smaller.

According to some embodiments, the acid is any appropriate acid in an aqueous solution, such as HCl, $H_2SO_4$, $H_3PO_4$, $HNO_3$, $C_6H_8O_7$, $H_2CO_3$, $H_3BO_3$, or any combination thereof. It is noted that the concentrations of the acids may be determined by the required pH, and may be dependent on the Ka of the particular acid used, such that the stronger the acid, the lower the concentration thereof used.

According to some embodiments, the pH of the acidic solution is between about 2-4. According to some embodiments, the pH of the acidic solution is between about 2-3. According to some embodiments, the pH of the acidic solution is between about 3-4. According to some embodiments, the pH of the acidic solution is between about 2.5-3.5. According to some embodiments, the pH of the acidic solution is about 3.

According to some embodiments, the base is any appropriate base in aqueous solution, such as NaOH, $NaHCO_3$, KOH, $NH_4OH$, $Ca(OH)_2$, or any combination thereof. It is noted that the concentrations of the bases may be determined by the required pH, and may be dependent on the Kb of the particular base used, such that the stronger the base, the lower the concentration thereof used.

According to some embodiments, the pH of the basic solution is between about 11-14. According to some embodiments, the pH of the basic solution is between about 11-12. According to some embodiments, the pH of the basic solution is between about 12-13. According to some embodiments, the pH of the basic solution is between about 13-14. According to some embodiments, the pH of the basic solution is between about 11.5-12.5. According to some embodiments, the pH of the basic solution is about 12.

According to some embodiments, the basic or acidic aqueous solution is heated to a temperature of between about 50-95° C. According to some embodiments, the basic or acidic aqueous solution is heated to a temperature of between about 50-60° C. According to some embodiments, the basic or acidic aqueous solution is heated to a temperature of between about 60-70° C. According to some embodiments, the basic or acidic aqueous solution is heated to a temperature of between about 70-80° C. According to some embodiments, the basic or acidic aqueous solution is heated to a temperature of between about 80-90° C. According to some embodiments, the basic or acidic aqueous solution is heated to a temperature of between about 90-95° C.

According to some embodiments, co-crystallization of anhydrous guanine and at least one additional material is induced by cooling the basic or acidic aqueous solution at a predetermined rate of between about 0.1-5.0 degrees/minute. According to some embodiments, co-crystallization of anhydrous guanine and at least one additional material is induced by cooling the basic or acidic aqueous solution at a predetermined rate of between about 0.1-1.0 degrees/minute. According to some embodiments, co-crystallization of anhydrous guanine and at least one additional material is induced by cooling the basic or acidic aqueous solution at a predetermined rate of between about 1.0-2.0 degrees/minute. According to some embodiments, co-crystallization of anhydrous guanine and at least one additional material is induced by cooling the basic or acidic aqueous solution at a predetermined rate of between about 2.0-3.0 degrees/minute. According to some embodiments, co-crystallization of anhydrous guanine and at least one additional material is induced by cooling the basic or acidic aqueous solution at a predetermined rate of between about 3.0-4.0 degrees/minute. According to some embodiments, co-crystallization of anhydrous guanine and at least one additional material is induced by cooling the basic or acidic aqueous solution at a predetermined rate of between about 4.0-5.0 degrees/minute.

According to some embodiments, crystallization of anhydrous guanine is induced by cooling the basic or acidic aqueous solution at a predetermined rate of between about 0.1-5.0 degrees/minute. According to some embodiments, crystallization of anhydrous guanine is induced by cooling the basic or acidic aqueous solution at a predetermined rate of between about 0.1-1.0 degrees/minute. According to some embodiments, crystallization of anhydrous guanine is induced by cooling the basic or acidic aqueous solution at a predetermined rate of between about 1.0-2.0 degrees/minute. According to some embodiments, crystallization of anhydrous guanine is induced by cooling the basic or acidic aqueous solution at a predetermined rate of between about 2.0-3.0 degrees/minute. According to some embodiments, crystallization of anhydrous guanine is induced by cooling the basic or acidic aqueous solution at a predetermined rate of between about 3.0-4.0 degrees/minute. According to some embodiments, crystallization of anhydrous guanine is induced by cooling the basic or acidic aqueous solution at a predetermined rate of between about 4.0-5.0 degrees/minute.

According to some embodiments, the basic or acidic aqueous solution is cooled to a predetermined temperature of about 4-20° C. According to some embodiments, the basic or acidic aqueous solution is cooled to a predetermined temperature of about 4-10° C. According to some embodiments, the basic or acidic aqueous solution is cooled to a predetermined temperature of about 10-15° C. According to some embodiments, the basic or acidic aqueous solution is cooled to a predetermined temperature of about 15-20° C.

Figure 1B:
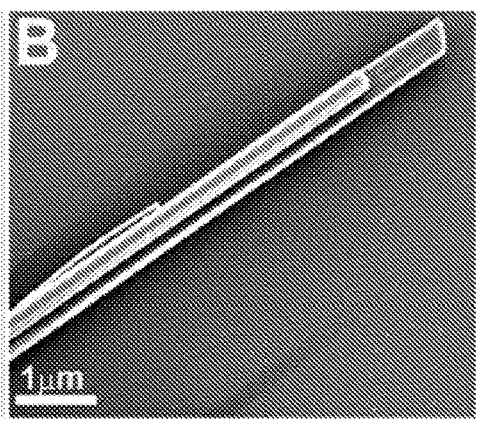
Figure 1C:
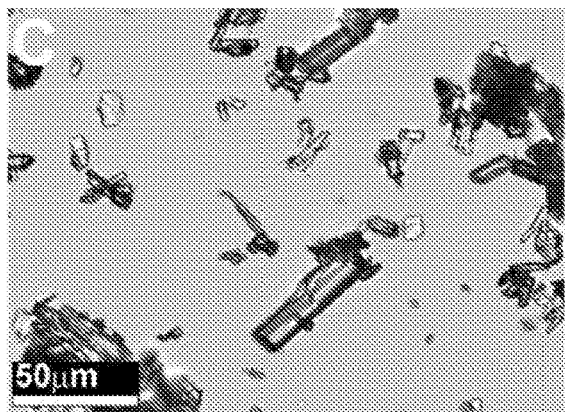
FIGS. 1C and 1D present elongated crystals having a bulky prismatic appearance prepared under basic conditions.
Figure 1D:
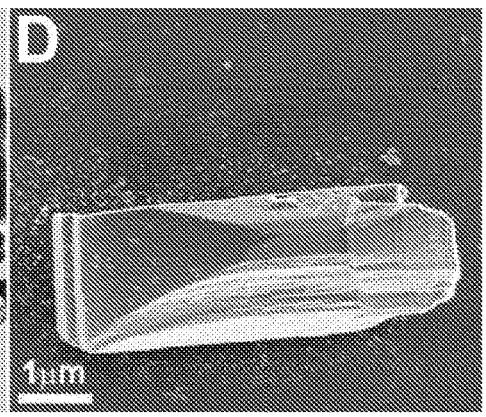
Figure 2A:
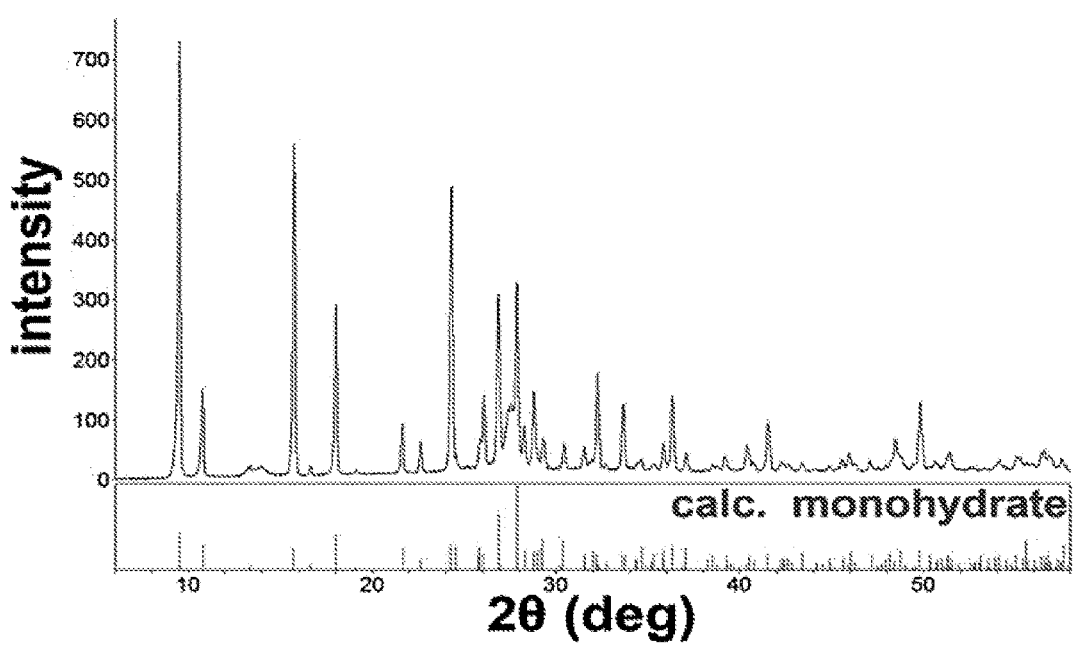
FIG. 2A presents the X-ray powder diffraction of anhydrous guanine the phase, obtained at pH=2, of the elongated acicular crystals of guanine monohydrate.
Figure 2B:
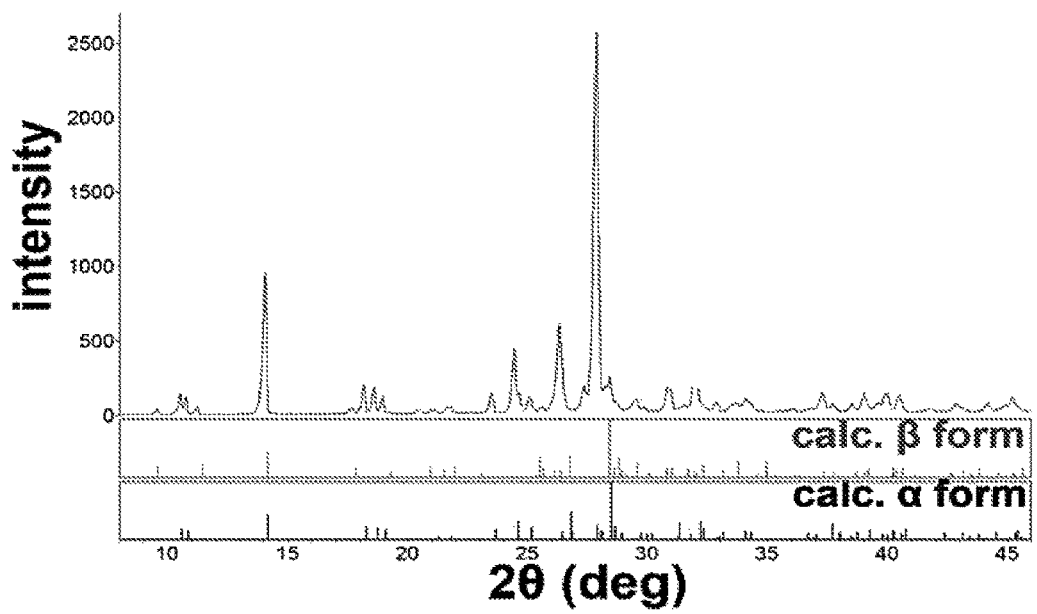
FIG. 2B presents the X-ray powder diffraction of the phase, obtained at pH=11, of the elongated crystals having a bulky prismatic appearance of α and β polymorphs of anhydrous guanine.
Figure 2C:
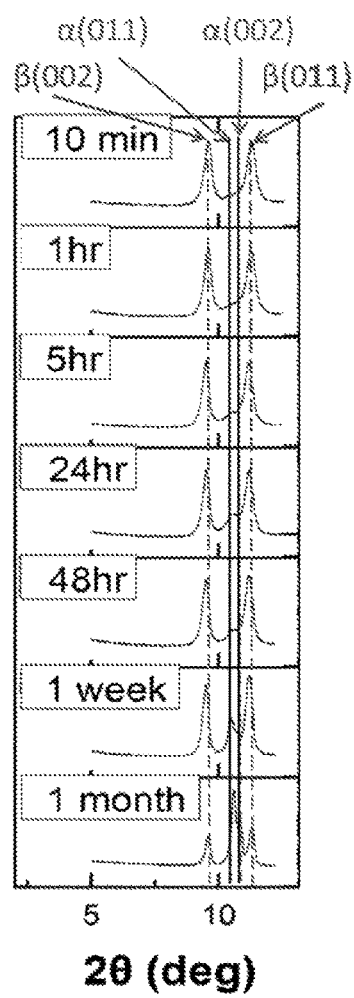
FIG. 2C presents the evolution in time of the anhydrous guanine polymorphs in suspension.

Embodiments of the invention are further directed to the preparation of various guanine phases, including anhydrous guanine and guanine monohydrate, as well as transforming guanine monohydrate to anhydrous guanine. As shown by the X-ray powder diffraction results presented in FIGS. 2A-2C, the elongated acicular crystals are guanine monohydrate crystals (See FIG. 2A, presenting the X-ray powder diffraction of the phase obtained at pH=2 and SEM pictures in FIGS. 1A and 1B. The phase presented in FIG. 2A was obtained by filtration of the monohydrate about 10 minutes after the crystals were obtained, such that the monohydrate would not be transformed into the anhydrous phase; however, the spectrum itself was obtained after 24 hours), while the crystals with prismatic bulky morphology are α and β polymorphs of anhydrous guanine (see FIG. 2B, presenting the X-ray powder diffraction of the phase obtained at pH=11, and SEM pictures in FIGS. 1C and 1D. The phase presented in FIG. 2B was obtained by filtration of the anhydrous form about 16 hours after the crystals were obtained; however, the spectrum itself was obtained after 24 hours). It is noted that the differences in the filtration times of the monohydrate and the anhydrous forms, as presented in FIGS. 2A and 2B, respectively, stem from the differences in the rate of transformation from the monohydrate to the anhydrous form under different pH conditions. FIG. 2C presents the evolution in time of the anhydrous guanine polymorphs in suspension, followed through the intensity of the (011) and (002) diffraction peaks in the α polymorph (solid lines) and in the β polymorph (dashed lines). Initially the suspension consists of the pure β form, which in time transforms into the α form.

Figure 4A:
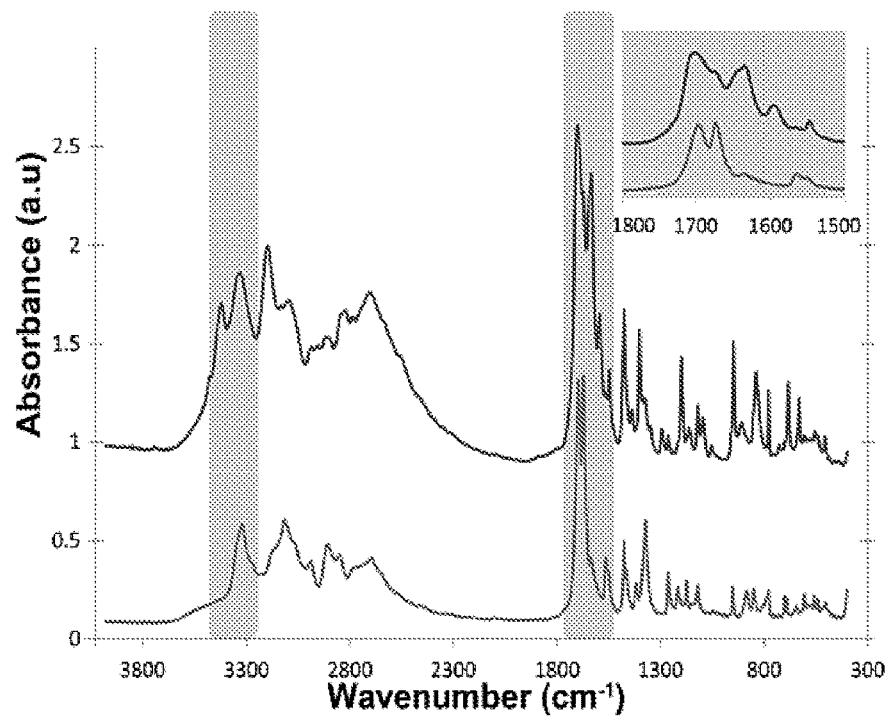
FIG. 4A presents FTIR spectra of anhydrous guanine (gray line) and guanine monohydrate (black line)
Figure 4B:
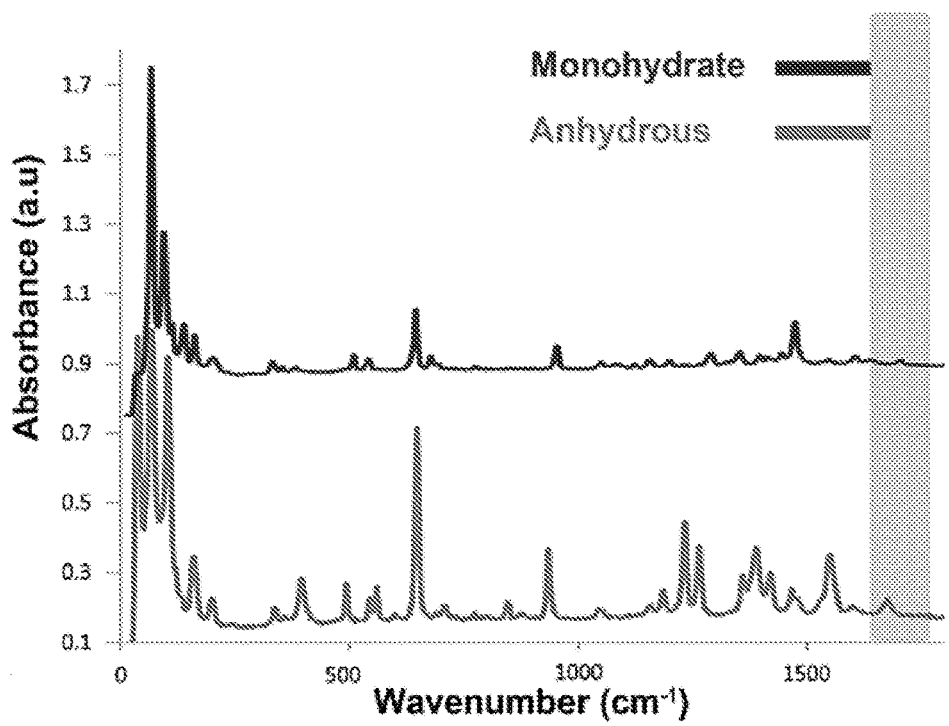
FIG. 4B presents Raman spectra of anhydrous guanine (gray line) and guanine monohydrate (black line).

FTIR spectrum of guanine monohydrate is distinctly different from the spectrum of anhydrous guanine (FIG. 4A). Most evident differences are: i) The broad peaks at 3420 and 3200 $cm^{-1}$ and the peak at 1596 $cm^{-1}$, corresponding to the water stretching modes υ1 and υ3, and the bending mode υ2 respectively, which are present in the monohydrate but not in the anhydrous phase; ii) The C=O and $NH_2$ stretching vibrations appear as multiple peaks between 1633-1705 $cm^{-1}$ in the monohydrate phase, whereas they appear as two resolved peaks at 1695 and 1672 $cm^{-1}$ in the anhydrous phase. The Raman spectrum of guanine monohydrate is also distinctly different from the spectrum of anhydrous guanine (FIG. 4B). Several vibrations are shifted: specifically, the C=O peak at 1675 $cm^{-1}$ in the anhydrous phase shifts to 1702 $cm^{-1}$ in the guanine monohydrate phase.

Figure 6:
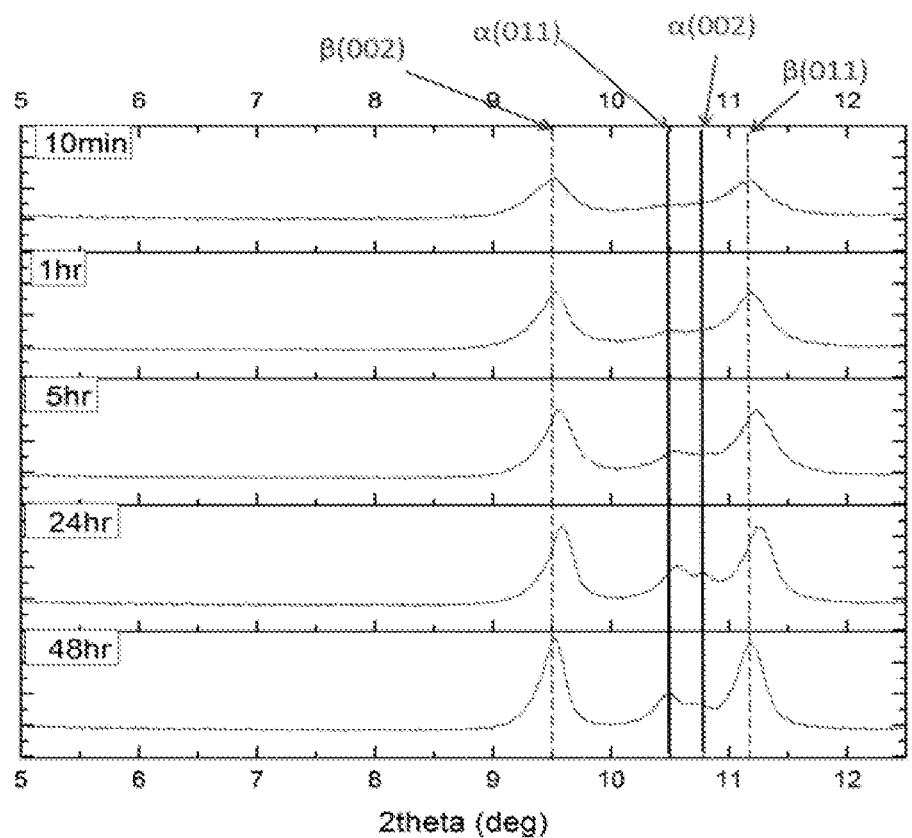
FIG. 6 presents X-ray powder diffraction patterns. Evolution in time of the anhydrous guanine polymorphs in a pH 7 suspension, followed through the intensity of the (011) and (002) diffraction peaks in the α polymorph (solid lines) and in the β polymorph (dashed lines). Initially the suspension consists of the pure β form, which in time transforms into the α form.
Figures 7A, 7B:
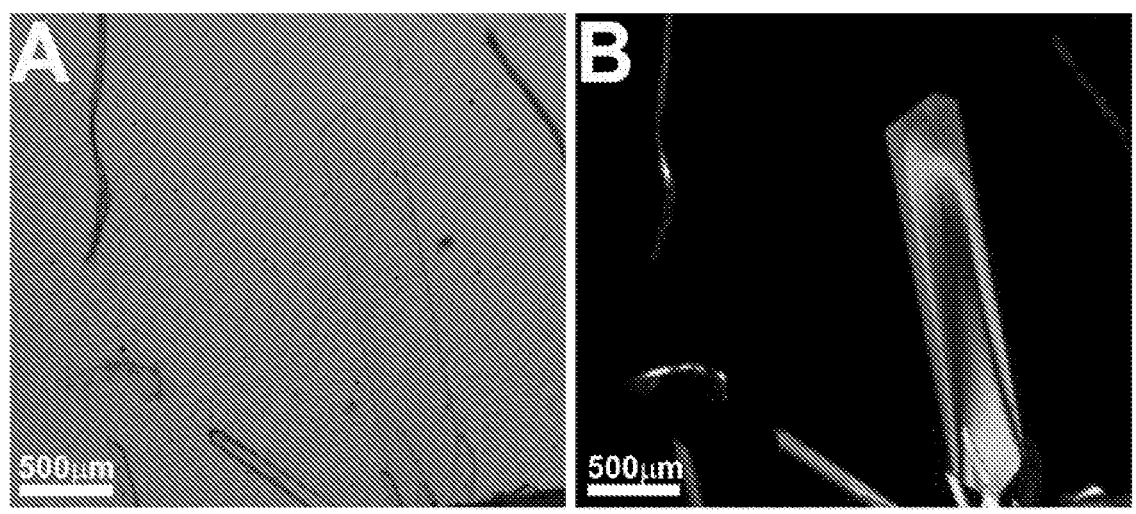
FIGS. 7A, 7B and 7C present disodium guanine heptahydrate salt. Recrystallization from solution at pH 14 results in the formation of disodium guanine heptahydrate.
Figure 7C:
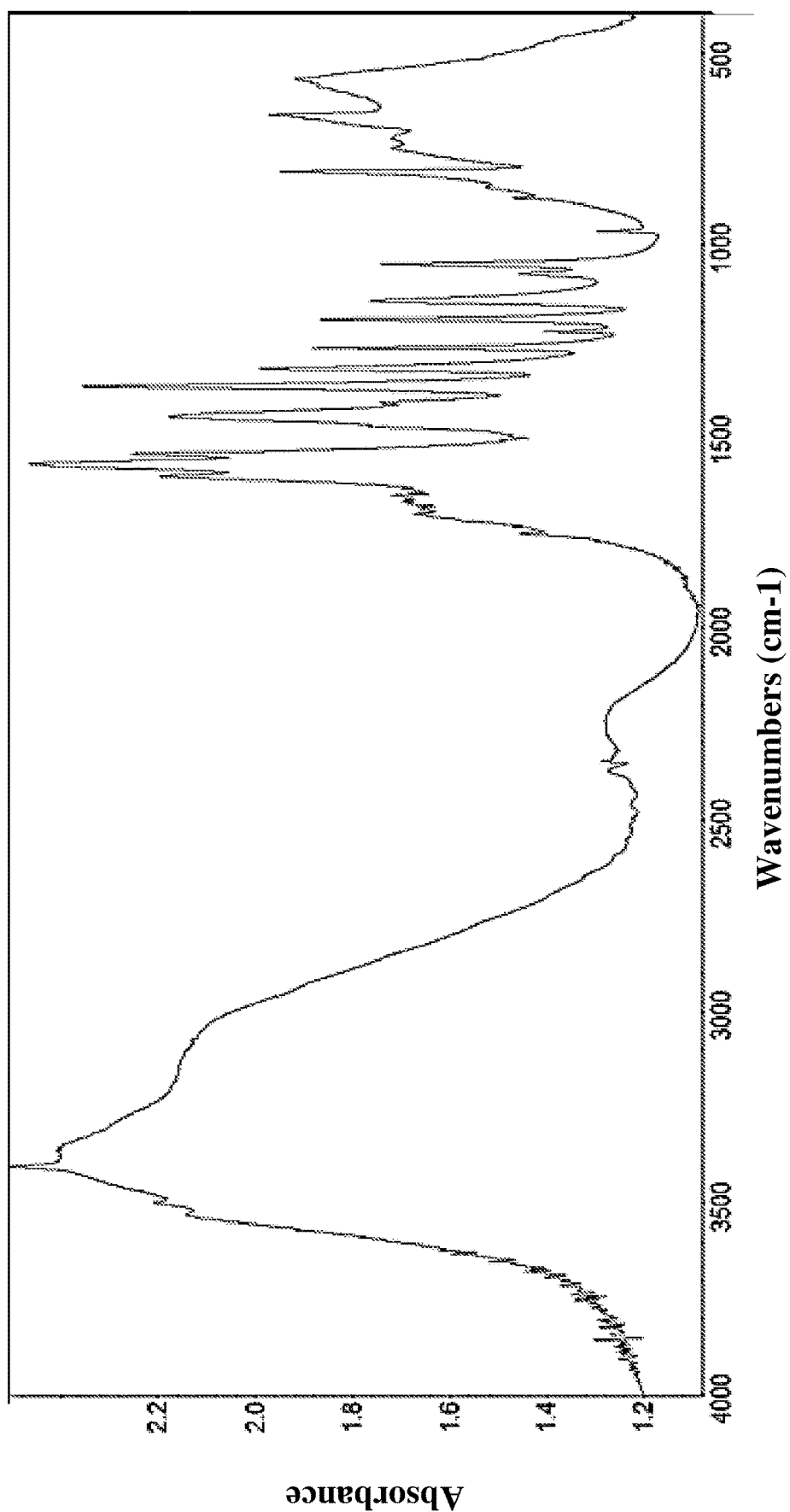

According to some embodiments, when the solution is highly basic, e.g., the pH is approximately 14, disodium guanine heptahydrate salt is obtained (FIGS. 7A-7C). According to some embodiments, guanine monohydrate is obtained from highly acidic solutions, e.g., when the pH is between about 1-3. According to some embodiments, when the pH is between about 4-6, a mixture of guanine monohydrate and anhydrous guanine is obtained. According to some embodiments, when the pH is between about 7-13 mainly anhydrous guanine is formed. According to some embodiments, the kinetically favored polymorph of anhydrous guanine is the β form, which in water suspension transforms with time into the α form (FIG. 2C), wherein the higher the pH the slower the transformation is (FIG. 6). It is noted that the transformation requires dissolution-reprecipitation, as demonstrated by the fact that material does not transform when kept dry.

As noted herein, the high refractive index of guanine is provided by large, plate crystals, and therefore, the control of the crystal size may be essential. According to some embodiments, when performing pH induced crystallization, the interplay between the initial guanine concentration, final guanine concentration, initial pH, final pH and the rate of lowering the pH may allow substantial control over the crystallization process as well as the crystal size. According to some embodiments, the pH is adjusted slowly, e.g., dropwise. According to some embodiments, the concentration of the guanine is relatively low, e.g., between about 0.003-0.2M. According to some embodiments, the concentration of the guanine is about 0.013M. Possibly, the low concentration of guanine and/or the slow adjustment of pH induces fewer nucleation events and therefore, large crystals, having an average size between about 5-1000 µm, are formed. According to some embodiments, at high concentration of guanine, between about 0.1-0.2M, and when the pH is rapidly adjusted, e.g., by adding the acid/base in one dose, the formation of small crystals, having an average size between about 0.01-10 µm, is induced.

Further embodiments of the invention are directed to a temperature controlled process for preparing crystalline anhydrous guanine, wherein said process comprises the steps of:

heating a crystalline powder of guanine monohydrate to a temperature of between 90-250° C.; and collecting the crystalline anhydrous guanine.

Figure 3A:
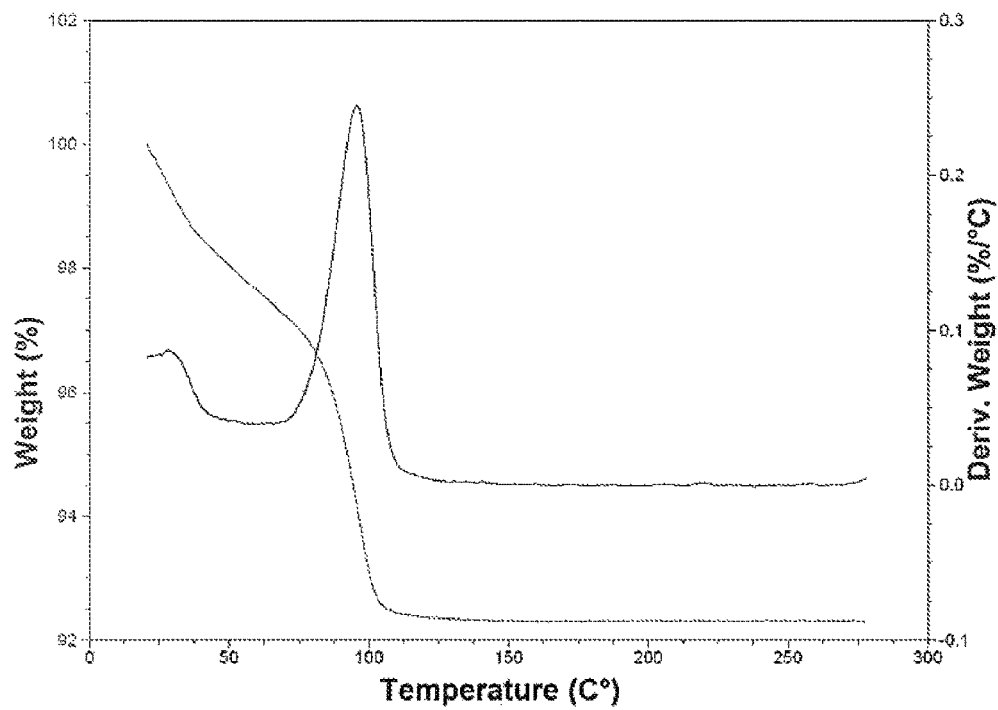
FIG. 3A presents the thermogravimetric analysis (TGA) spectra, showing the transformation of guanine monohydrate to anhydrous guanine upon heating.
Figure 3B:
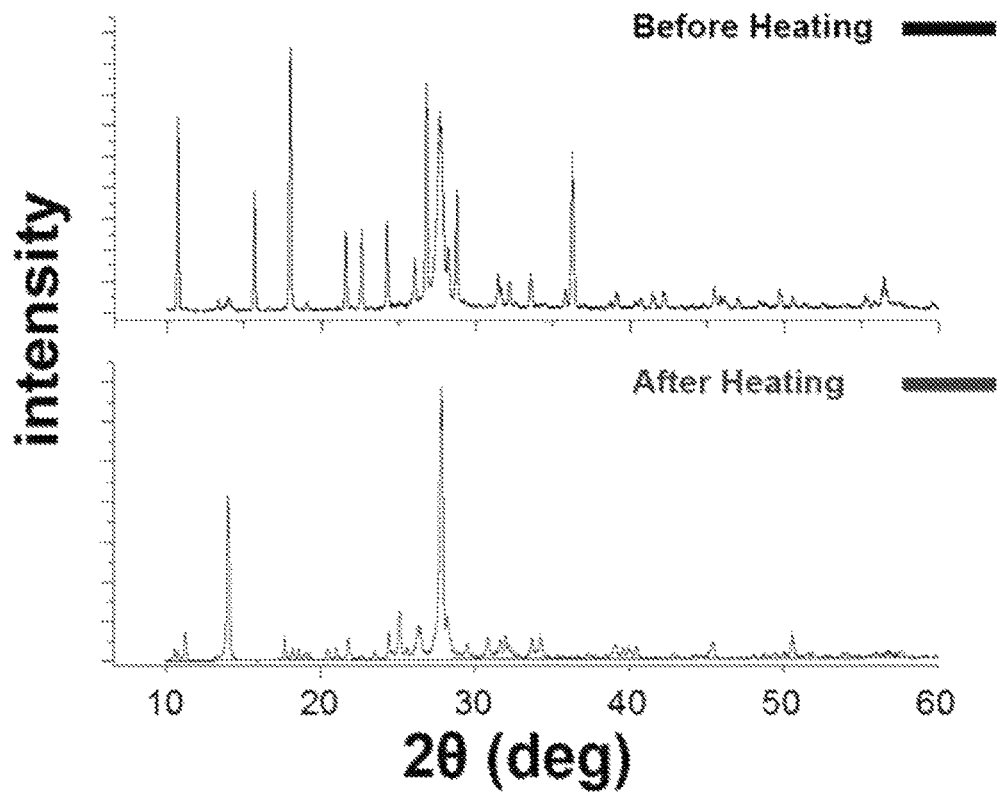
FIG. 3B presents the X-ray powder diffraction of the guanine before and after transformation from the monohydrate to the anhydrous form.
Figure 3C:
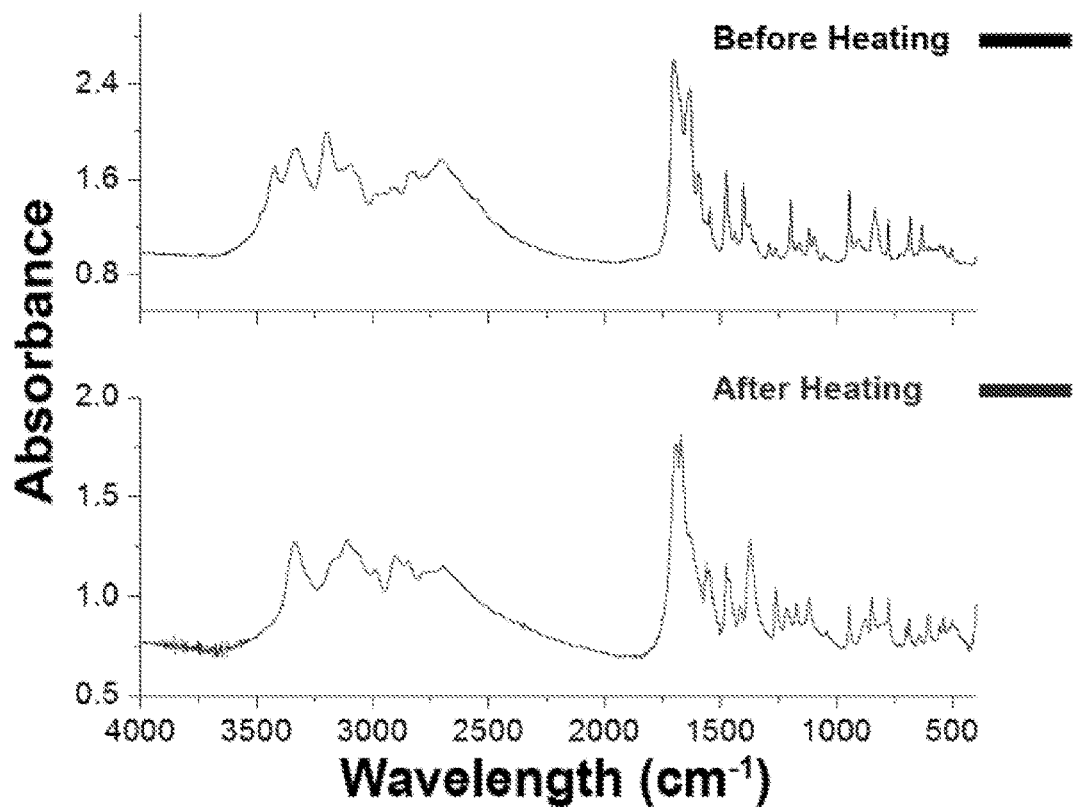
FIG. 3C presents the FTIR spectra of the guanine before and after transformation from the monohydrate to the anhydrous form.

According to some embodiments, crystalline anhydrous guanine is prepared by heating crystalline powder of guanine monohydrate. In another embodiment, without being bound by any mechanism or theory, it is suggested that the heating may remove the water molecules from the guanine monohydrate and subsequently induce phase transformation into anhydrous guanine. According to some embodiments, guanine monohydrate is heated to about 90-100° C., resulting in the deposition of aggregates of polycrystalline or crystalline anhydrous guanine, having acicular morphology. In another embodiment, guanine monohydrate is heated to about 100-150° C. In another embodiment, guanine monohydrate is heated to about 150-200° C. In another embodiment, guanine monohydrate is heated to about 200-250° C. FIG. 3A presents the TGA spectra, showing the transformation of guanine monohydrate to anhydrous guanine upon heating. FIG. 3B presents the X-ray powder diffraction of the guanine before and after transformation from the monohydrate to the anhydrous form after heating the sample to 250° C. for 10 minutes. FIG. 3C presents the FTIR spectra of the guanine before and after transformation from the monohydrate to the anhydrous form after heating the sample to 250° C. for 10 minutes. It is noted that although the samples presented in FIGS. 3B and 3C were heated to 250° C. it is possible, as detailed herein, to heat such samples to about 95° C.

According to some embodiments, if the crystals are kept in the crystal suspension, the transformation from monohydrate to anhydrous crystals may occur at room temperature within a few hours. It is noted that the term "suspension" in this respect is directed to the solution in which the crystals are formed and suspended in. Possibly, the transformation within the suspension occurs through the dissolution of guanine monohydrate and the formation of anhydrous guanine. In acidic conditions the crystals of guanine monohydrate may grow rapidly and may be the first to form in the solution, while the crystals of anhydrous guanine take much longer to form. If the suspension is not filtered and dried, anhydrous crystals may continue to grow at the expense of the dissolving guanine monohydrate crystals. A suspension which initially contains almost exclusively guanine monohydrate crystals may become a mixture of both phases within 10 minutes and may contain almost only anhydrous guanine within a few hours, wherein the transformation rate is dependent, e.g., on the concentration of the solution as well as the pH thereof. For example, when the pH is highly acidic, e.g., pH=1-2, the transformation to the anhydrous form may be at a lower rate than when using the same concentrations at a higher pH.

Figure 5:
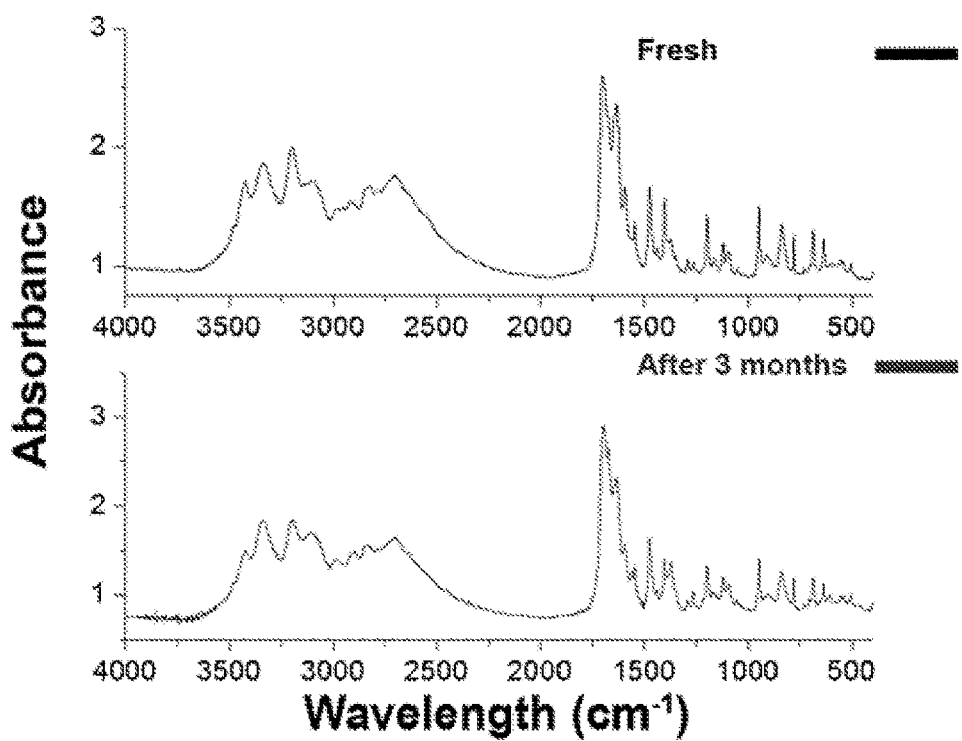
FIG. 5 presents FT-IR spectra, showing fresh guanine monohydrate (top) vs 3 months old guanine monohydrate. Only small differences in the peak intensities are visible after 3 months. The typical signatures of structured water are still present ($\upsilon 1$, and $\upsilon 3$ stretching modes (broad peaks at 3420 and 3200 cm$^{-1}$) and $\upsilon 2$ bending mode (1596 cm$^{-1}$)).

However, when stored dry at ambient conditions, guanine monohydrate is stable for at least several months and no solid to solid transformation occurs (FIG. 5).

In one embodiment, the process for the preparation of the co-crystals of this invention and the process for the preparation of the anhydrous guanine are carried out without the use of surfactant.

Further embodiments of the invention are directed to the synthetic co-crystal and anhydrous guanine prepared according to the process of the invention for use in paints including, but not limited to, wall paints and car paints, coatings, including, but not limited to, plastic coatings, glass coatings, ceramic coatings, and hydrophobic coating, printing inks, plastics, cosmetic formulations including, but not limited to, nail varnish, lipstick, mascara, and eyeliner, food products, paper, agricultural products, and medicaments.

Additional embodiments of the invention are directed to paints including, but not limited to, wall paints and car paints, coatings, including, but not limited to, plastic coatings, glass coatings, ceramic coatings, and hydrophobic coating, printing inks, plastics, cosmetic formulations including, but not limited to, nail varnish, lipstick, mascara, and eyeliner, food products, paper, agricultural products, and medicaments comprising the synthetic co-crystal of the invention and the anhydrous quinine prepared according to the process of this invention.

The plate like co-crystals of this invention provide both pearlescent and/or whiteness. Using larger particles (preferably larger than 10 µm) will provide a strongerpearlescent effect and using smaller particles (smaller than 10 µm) will provide a whiteness with high coverage.

The cosmetic compositions of this invention comprising the synthetic co-crystals of this invention and the anhydrous guanine prepared according to the process of this invention comprise white natural pigments having high coverage.

The coverage measurements (contrast ratio) for different pigments can be calculated as described in WO2014097134 using the following equation:

$$CR = \frac{\mathrm{mean}(Yblack)}{\mathrm{mean}(Ywhite)} \cdot 100$$

wherein Y is defined as luminance as in the CIE 1931 color space model.

The greater the percentage of the contrast ratio, the greater the opaqueness of the samples.

In one embodiment, the contrast ratio of the synthetic co-crystals of this invention and the anhydrous guanine prepared according to the process of this invention is between 20-60%.

Throughout this document, the term "about" is defined to include ±10% of the disclosed value.

In order to better understand how the present invention may be carried out, the following examples are provided, demonstrating a process according to the present disclosure.

EXAMPLES

Example 1

A Process of Preparing Guanine and Hypoxanthine Co-Crystal

A solution of 95% guanine and 5% hypoxanthine (mol/mol) was prepared by dissolving 14.3 mg of guanine powder (Sigma Aldrich) together with 0.70 mg of hypoxanthine (Sigma Aldrich) in 10 ml solution of NaOH (0.1M, pH 13), to provide a solution having concentrations of $9.5 \times 10^{-3}$ M guanine and $5.1 \times 10^{-4}$ M of hypoxanthine. The solution was mixed for 15 minutes, at a temperature of 25° C. The solution was then filtered using a PVDF filter, and 0.01 ml of 0.1 M NaOH were added to the solution to ensure that all of the powder was dissolved. Next, 0.9 ml of 1M HCl solution was added dropwise while stirring at a rate of 0.5 ml\min. Further, ~0.8 ml of 0.1 M HCl solution was added dropwise while stirring at a rate of 0.1 ml\min, until the pH of the solution was 11. The solution was matured for 20 hours, after which crystals were isolated therefrom by filtration with a PVDF membrane. The obtained crystals were the typical bulky 20-100 µm prismatic crystals obtained for anhydrous guanine.

Example 2

A Process of Preparing Small (~4 µm×0.5 µm) Anhydrous Guanine and Hypoxanthine Co-Crystals A solution of 25% guanine and 75% hypoxanthine (mol/mol) was prepared by dissolving 37.8 mg of guanine powder (Sigma Aldrich) together with 102.1 mg of hypoxanthine (Sigma Aldrich) in 10 ml solution of NaOH (0.1M, pH 13), to provide a solution having concentrations of $2.50 \times 10^{-2}$ M guanine and $7.50 \times 10^{-2}$ M of hypoxanthine. The solution was then mixed for 15 minutes, at a temperature of 25° C. The solutions were then filtered using a PVDF filter and 0.01 ml of 0.1 M NaOH were added to the solution to ensure that all of the powder was dissolved. Next, 0.95 ml of 1M HCl solution was added dropwise while stirring at a rate of 0.5 ml\min. Further, ~0.8 ml of 0.1 M HCl solution was added dropwise while stirring at a rate of 0.1 ml\min, until the pH of the solution was 10.5. The solution was matured for 20 hours, after which crystals were isolated therefrom by filtration with a PVDF membrane. The obtained co-crystals have plate morphology as shown in FIG. 8C with a refractive index of ~1.8. FIG. 8B presents the X-ray powder diffraction of the obtained co-crystals, showing a noticeable shift from pure anhydrous guanine. Moreover, the co-crystals have a preferred orientation, as is evident from the higher ratio of the intensity of the (100) to the (012) diffraction peaks.

It is apparent from comparing the results of Examples 1 and 2 that the formation of guanine-hypoxanthine co-crystals is dependent on the concentration ratio of the guanine and the hypoxanthine.

Example 3

A Process of Preparing Large (~40 µm×5 µm) Anhydrous Guanine and Hypoxanthine Co-Crystals A solution of 25% guanine and 75% hypoxanthine (mol/mol) was prepared by dissolving 9.45 mg of guanine powder (Sigma Aldrich) together with 25.53 mg of hypoxanthine (Sigma Aldrich) in 10 ml solution of NaOH (0.1M, pH 13), to provide a solution having concentrations of $0.625 \times 10^{-2}$ M guanine and $1.875 \times 10^{-2}$ M of hypoxanthine. The solution was then mixed for 15 minutes, at a temperature of 25° C. The solutions were then filtered using a PVDF filter and 0.01 ml of 0.1 M NaOH were added to the solution to ensure that all of the powder was dissolved. Next, 0.8 ml of 1M HCl solution was added dropwise while stirring at a rate of 0.5 ml\min. Further, ~0.5 ml of 0.1 M HCl solution was added dropwise while stirring at a rate of 0.1 ml\min, until the pH of the solution was 11. The solution was matured for 20 hours, after which crystals 40 µm long and 5 µm with excellent pearlescent properties were isolated therefrom by centrifugation.

Example 4

A Process of Preparing Guanine and Guanosine Co-Crystal

A solution of 90% guanine and 10% guanosine (mol/mol) was prepared by dissolving 378.0 mg of guanine powder (Sigma Aldrich) together with 78.5 mg of guanosine (Sigma Aldrich) in 100 ml solution of NaOH (0.1 M, pH 13), to provide a solution having concentrations of $2.50 \times 10^{-2}$ M guanine and $2.77 \times 10^{-3}$ M of guanosine. The solution was then mixed for 15 minutes, at a temperature of 40° C. The solutions were then filtered using a PVDF filter and 0.1 ml of 0.1 M NaOH were added to the solution to ensure that all of the powder was dissolved. Next, 9.0 ml of 1M HCl solution was added dropwise while stirring at a rate of 5.0 ml\min. Further, ~8.0 ml of 0.1 M HCl solution was added dropwise while stirring at a rate of 0.5 ml\min, until the pH of the solution was 11. The solution was matured for 12 hours, after which crystals were isolated using centrifugation (10 min at 6400 RPM). The obtained co-crystals had plate morphology with a high refractive index of ~1.8.

Example 5

A Process of Preparing Guanine and Xanthine Co-Crystal

A solution of 50% guanine and 50% xanthine (mol/mol) was prepared by dissolving 250.0 mg of guanine powder (Sigma Aldrich) together with 243.0 mg of xanthine (Sigma Aldrich) in 100 ml solution of NaOH (0.1 M, pH 13), to provide a solution having concentrations of $1.60 \times 10^{-2}$ M for both guanine and xanthine. The solution was then mixed for 30 minutes, at a temperature of 25° C. Next, 10.0 ml of 1M HCl solution was added dropwise while stirring at a rate of 5.0 ml\min. Further, ~7.0 ml of 0.1 M HCl solution was added dropwise while stirring at a rate of 0.5 ml\min, until the pH of the solution was 10. The solution was matured for 8 hours, after which crystals were isolated using centrifugation (10 min at 6400 RPM). The obtained co-crystals had plate morphology with a high refractive index of ~1.8.

Example 6

A Process of Preparing Anhydrous Guanine Crystals

A Guanine solution was prepared by dissolving 37.8 mg of guanine powder (Sigma Aldrich) in 10 ml solution of NaOH (0.1M, pH 13). The solution was then mixed for 15 minutes, at a temperature of 25° C. The solution was then filtered using a PVDF filter and 0.01 ml of 0.1 M NaOH were added to the solution to ensure that all of the powder was dissolved. Next, 0.95 ml of 1M HCl solution was added dropwise while stirring at a rate of 0.5 ml\min. Further, ~0.8 ml of 0.1 M HCl solution was added dropwise while stirring at a rate of 0.1 ml\min, until the pH of the solution was 10.5. The solution was matured for 24 hours, after which crystals were isolated therefrom by centrifugation. The obtained crystals had a bulky prismatic morphology as shown in FIGS. 1C and D. FIG. 2B presents the X-ray powder diffraction of the obtained crystals, showing a typical pattern of anhydrous guanine crystals.

Example 7

A Nail Composition Comprising the Co-Crystal or the Anhydrous Guanine of this Invention 97% by weight of thixotropic nail varnish base 1348 (International Laquers S.A., comprising toluene, ethyl acetate, ethyl acetate, nitrocellulose, tosylamide-formaldehyde resin, dibutyl phthalate, isopropanol, stear-alkonium hectorite, camphor, acrylate copolymer, benzophenone) and 3% by weight of a dispersion of 11% by weight of plates of guanine-hypoxanthine co-crystals (prepared according to the procedure detailed in Example 2) or the anhydrous guanine (prepared according to the process of claim 5) in castor oil are mixed by hand using a spatula and subsequently stirred at 1000 rpm for 10 min. A nail varnish having uniform luster is obtained.

Example 8

A Lipstick Composition Comprising the Co-Crystal or the Anhydrous Guanine of this Invention A lipstick composition comprising the co-crystal of this invention (prepared according to Examples 1-5) or the anhydrous guanine (prepared according to the process of Example 6) is prepared as described in WO 2014097134.

Example 9

A Thermal Process which Provides the Anhydrous Guanine of this Invention

A crystalline powder of guanine monohydrate was heated to 250° C. FIG. 3A presents the TGA spectra, showing the transformation of crystalline guanine monohydrate to crystalline anhydrous guanine upon heating. FIG. 3B presents the X-ray powder diffraction of the crystalline guanine before and after transformation from the monohydrate to the anhydrous form after heating the sample to 250° C. for 10 minutes. FIG. 3C presents the FTIR spectra of the crystalline guanine before and after transformation from the monohydrate to the anhydrous form after heating the sample to 250° C. for 10 minutes.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. Synthetic co-crystals comprising anhydrous guanine and at least one additional material; wherein the at least one additional material is guanosine, and wherein the co-crystals have a plate morphology.

2. The synthetic co-crystals according to claim 1, having a refractive index between 1.75-1.86.

3. Paints, coatings, printing inks, plastics, cosmetic formulations, food products, paper, agricultural products, and medicaments, comprising the synthetic co-crystal according to claim 1.

4. Synthetic co-crystals consisting of anhydrous guanine and one additional material; wherein the one additional material is selected from the group consisting of hypoxanthine, xanthine and guanosine, wherein the co-crystals have a plate morphology.

5. The synthetic co-crystals according to claim 4, wherein the one additional material is hypoxanthine or xanthine.

6. The synthetic co-crystals according to claim 4, wherein the one additional material is guanosine.

7. The synthetic co-crystals according to claim 4, having a refractive index between 1.75-1.86.

8. The synthetic co-crystals according to claim 4, wherein said co-crystals are 5-250 μm long and/or 1-50 μm wide and/or 20-500 nm thick.

9. The synthetic co-crystals according to claim 4, wherein said co-crystals have an average size of about 0.01-10 μm.

10. The synthetic co-crystals according to claim 4, wherein said co-crystals have a smooth surface.

11. The synthetic co-crystals according to claim 5, wherein the one additional material is hypoxanthine.

12. The synthetic co-crystals according to claim 11, wherein the co-crystals are characterized by an X-ray powder diffraction having a noticeable shift from pure anhydrous guanine and higher ratio of the intensity of the (100) to the (012) diffraction peaks.

13. The synthetic co-crystals according to claim 11, wherein the co-crystals have a rectangular shape.

14. The synthetic co-crystals according to claim 11, wherein the co-crystals are free of impurities originating from crystals isolated from fish scales.

15. Paints, coatings, printing inks, plastics, cosmetic formulations, food products, paper, agricultural products, and medicaments, comprising the synthetic co-crystal according to claim 4.

16. A pH controlled process for preparing the synthetic co-crystals according to claim 1, wherein said process comprises the steps of:
preparing a basic or acidic aqueous solution of guanine and the at least one additional material;
maintaining the basic or acidic aqueous solution at a predetermined temperature range for a predetermined period of time;
filtering the basic or acidic aqueous solution to provide a filtrate;
adjusting the pH of the filtrate by adding a base or an acid to the filtrate over a predefined period of time until a predetermined pH value is obtained, thereby providing a synthetic co-crystal suspension comprising co-crystals;
allowing the synthetic co-crystal suspension to mature over a predetermined period of time; and
collecting the synthetic co-crystals from the crystal suspension.

17. The pH controlled process according to claim 16, wherein the molar ratio between the at least one additional material and guanine is between 4:1-0.01:1.

18. The pH controlled process according to claim 17, wherein the acid is selected from the group consisting of HCl, $H_2SO_4$, $H_3PO_4$, $HNO_3$, $C_6H_8O_7$, $H_2CO_3$, $H_3BO_3$, and any combination thereof and the pH of the acidic solution is between 0-3.

19. The pH controlled process according to claim 16, wherein the base is selected from the group consisting of NaOH, $NaHCO_3$, KOH, $NH_4OH$, $Ca(OH)_2$, and any combination thereof, and the pH of the basic solution is between 12-14.

20. The pH controlled process according to claim 16, wherein the pH of the filtrate is adjusted by dropwise adding a base or an acid to the filtrate over a period of time of 1-20 minutes, wherein the predetermined pH value is between 10.5-11.5.

21. A temperature controlled process for preparing the synthetic co-crystals according to claim 1, wherein said process comprises the steps of:
preparing a basic or acidic aqueous solution of guanine and the at least one additional material;
heating the basic or acidic aqueous solution to a predetermined temperature for the predetermined length of time;
inducing co-crystallization by cooling the basic or acidic aqueous solution at a predetermined rate until reaching a predetermined temperature thereby providing a synthetic co-crystal suspension comprising crystals;
allowing the synthetic co-crystal suspension to mature over a predetermined period of time; and
collecting the synthetic co-crystals from the crystal suspension.

22. A pH controlled process for preparing the synthetic co-crystals according to claim 4, wherein said process comprises the steps of:
preparing a basic or acidic aqueous solution of guanine and the one additional material;
maintaining the basic or acidic aqueous solution at a predetermined temperature range for a predetermined period of time;
filtering the basic or acidic aqueous solution to provide a filtrate;
adjusting the pH of the filtrate by adding a base or an acid to the filtrate over a predefined period of time until a predetermined pH value is obtained, thereby providing a synthetic co-crystal suspension comprising co-crystals;
allowing the synthetic co-crystal suspension to mature over a predetermined period of time; and
collecting the synthetic co-crystals from the crystal suspension.

23. The pH controlled process according to claim 22, wherein the molar ratio between the one additional material and guanine is between 4:1-0.01:1.

24. The pH controlled process according to claim 22, wherein the basic or acidic aqueous solution comprises 0.003-0.2M of guanine.

25. The pH controlled process according to claim 22, wherein the basic or acidic aqueous solution comprises 0.003-0.2M of the one additional material.

26. The pH controlled process according to claim 22, wherein the acid is selected from the group consisting of $HCl$, $H_2SO_4$, $H_3PO_4$, $HNO_3$, $C_6H_8O_7$, $H_2CO_3$, $H_3BO_3$, and any combination thereof.

27. The pH controlled process according to claim 22, wherein the pH of the acidic solution is between 0-3.

28. The pH controlled process according to claim 22, wherein the base is selected from the group consisting of $NaOH$, $NaHCO_3$, $KOH$, $NH_4OH$, $Ca(OH)_2$, and any combination thereof.

29. The pH controlled process according to claim 22, wherein the pH of the basic solution is between 12-14.

30. The pH controlled process according to claim 22, wherein the pH of the filtrate is adjusted by dropwise adding a base or an acid to the filtrate over a period of time of 1-20 minutes.

31. The pH controlled process according to claim 22, wherein the predetermined pH value is between 10.5-11.5.

32. A temperature controlled process for preparing the synthetic co-crystals according to claim 4, wherein said process comprises the steps of:
preparing a basic or acidic aqueous solution of guanine and the one additional material;
heating the basic or acidic aqueous solution to a predetermined temperature for the predetermined length of time;
inducing co-crystallization by cooling the basic or acidic aqueous solution at a predetermined rate until reaching a predetermined temperature thereby providing a synthetic co-crystal suspension comprising crystals;
allowing the synthetic co-crystal suspension to mature over a predetermined period of time; and
collecting the synthetic co-crystals from the crystal suspension.

* * * * *